(12) United States Patent
Valadez et al.

(10) Patent No.: US 9,741,131 B2
(45) Date of Patent: Aug. 22, 2017

(54) ANATOMY AWARE ARTICULATED REGISTRATION FOR IMAGE SEGMENTATION

(71) Applicants: Siemens Medical Solutions USA, Inc., Malvern, PA (US); Siemens Aktiengesellscaft, Munich (DE)

(72) Inventors: Gerardo Hermosillo Valadez, West Chester, PA (US); Yiqiang Zhan, West Chester, PA (US); Xiang Sean Zhou, Exton, PA (US); Matthias Fenchel, Erlangen (DE); Berthold Kiefer, Erlangen (DE)

(73) Assignees: Siemens Medical Solutions USA, Inc., Malvern, PA (US); Siemens Aktiengesellschaft, Munich (DE)

( * ) Notice: Subject to any disclaimer, the term of this patent is extended or adjusted under 35 U.S.C. 154(b) by 100 days.

(21) Appl. No.: 14/331,757

(22) Filed: Jul. 15, 2014

(65) Prior Publication Data
US 2015/0023575 A1 Jan. 22, 2015

Related U.S. Application Data

(60) Provisional application No. 61/847,175, filed on Jul. 17, 2013.

(51) Int. Cl.
*A61B 6/00* (2006.01)
*G06T 7/11* (2017.01)
*G06T 7/33* (2017.01)

(52) U.S. Cl.
CPC .............. *G06T 7/33* (2017.01); *A61B 6/5235* (2013.01); *G06T 7/11* (2017.01); *A61B 6/505* (2013.01); *G06T 2207/10081* (2013.01); *G06T 2207/10088* (2013.01); *G06T 2207/10104* (2013.01); *G06T 2207/30008* (2013.01)

(58) Field of Classification Search
None
See application file for complete search history.

(56) References Cited

U.S. PATENT DOCUMENTS

| 7,920,730 | B2 | 4/2011 | Jerebko |
| 8,488,857 | B2* | 7/2013 | Young et al. ................. 382/131 |
| 8,588,495 | B2 | 11/2013 | Gupta et al. |

(Continued)

FOREIGN PATENT DOCUMENTS

| WO | 2007/037848 | 4/2007 |
| WO | 2007/044527 | 4/2007 |
| WO | 2008/027393 | 3/2008 |

*Primary Examiner* — Michelle Hausmann

(57) ABSTRACT

Disclosed herein is a framework for facilitating image processing. In accordance with one aspect, the framework receives first image data acquired by a first modality and one or more articulated models. The one or more articulated models may include at least one section image acquired by the first modality and aligned with a local image acquired by a second modality. The framework may align an anatomical region of the first image data with the section image and non-rigidly register a first region of interest extracted from the section image with a second region of interest extracted from the aligned anatomical region. To generate a segmentation mask of the anatomical region, the registered first region of interest may be inversely mapped to a subject space of the first image data.

16 Claims, 12 Drawing Sheets

(56) References Cited

U.S. PATENT DOCUMENTS

| | | |
|---|---|---|
| 8,977,029 B2* | 3/2015 | Du .......................... G06T 7/174 |
| | | 382/131 |
| 2005/0201601 A1* | 9/2005 | Sun et al. ..................... 382/128 |
| 2006/0002630 A1* | 1/2006 | Fu et al. ....................... 382/294 |
| 2007/0081706 A1 | 4/2007 | Zhou et al. |
| 2008/0049999 A1 | 2/2008 | Jerebko et al. |
| 2008/0159607 A1* | 7/2008 | Littmann ...................... 382/128 |
| 2008/0161687 A1* | 7/2008 | Suri .................... A61B 8/0833 |
| | | 600/437 |
| 2008/0292194 A1* | 11/2008 | Schmidt et al. .............. 382/217 |
| 2009/0228299 A1* | 9/2009 | Kangarloo et al. ................ 705/2 |
| 2012/0140998 A1* | 6/2012 | Zhu ......................... G06T 5/006 |
| | | 382/128 |
| 2013/0223704 A1* | 8/2013 | Lay .......................... G06K 9/34 |
| | | 382/128 |
| 2015/0003696 A1* | 1/2015 | Matthews ..................... 382/128 |
| 2015/0016728 A1* | 1/2015 | Parthasarathy et al. ...... 382/195 |
| 2016/0163048 A1* | 6/2016 | Yee .......................... G06T 7/11 |
| | | 382/131 |

\* cited by examiner

ANATOMY AWARE ARTICULATED REGISTRATION FOR IMAGE SEGMENTATION

CROSS-REFERENCE TO RELATED APPLICATION

This application claims the benefit of U.S. provisional application No. 61/847,175 filed on Jul. 17, 2013, the entire contents of which are incorporated herein by reference.

TECHNICAL FIELD

The present disclosure generally relates to diagnostic imaging and, more specifically, to automated or semi-automated systems and methods for facilitating image segmentation based on anatomy-aware articulated registration.

BACKGROUND

The field of medical imaging has seen significant advances since the time X-Rays were first used to determine anatomical abnormalities. Medical imaging hardware has progressed from modern machines such as Medical Resonance Imaging (MRI) scanners, Computed Tomographic (CT) scanners, and Positron Emission Tomographic (PET) scanners, to multimodality imaging systems such as PET-CT and PET-MRI systems. Because of large amount of image data generated by such modern medical scanners, there has been and remains a need for developing image processing techniques that can automate some or all of the processes to determine the presence of anatomical abnormalities in scanned medical images.

Recognizing anatomical structures within digitized medical images presents multiple challenges. For example, a first concern relates to the accuracy of recognition of anatomical structures within an image. A second area of concern is the speed of recognition. Because medical images are an aid for a doctor to diagnose a disease or condition, the speed with which an image can be processed and structures within that image recognized can be of the utmost importance to the doctor in order to reach an early diagnosis. Hence, there is a need for improving recognition techniques that provide accurate and fast recognition of anatomical structures and possible abnormalities in medical images.

Digital medical images are constructed using raw image data obtained from a scanner, for example, a CAT scanner, MRI, etc. Digital medical images are typically either a two-dimensional ("2-D") image made of pixel elements or a three-dimensional ("3-D") image made of volume elements ("voxels"). Such 2-D or 3-D images are processed using medical image recognition techniques to determine the presence of anatomical abnormalities such as cysts, tumors, polyps, etc. Given the amount of image data generated by any given image scan, it is preferable that an automatic technique should point out anatomical features in the selected regions of an image to a doctor for further diagnosis of any disease or condition.

Automatic image processing and recognition of structures within a medical image is generally referred to as Computer-Aided Detection (CAD). A CAD system can process medical images and identify anatomical structures including possible abnormalities for further review. Such possible abnormalities are often called candidates and are considered to be generated by the CAD system based upon the medical images.

CAD systems may be used to process images acquired by PET imaging systems. PET a functional imaging technique that produces a three-dimensional image of functional processes in the body. As PET data is acquired, attenuation of some of the PET photons may occur. Attenuation can lead to degraded image quality and reduced quantitative accuracy. Accordingly, in certain situations, such as patient imaging, PET imaging is combined with X-ray computed tomography (CT) imaging to correct for such attenuation. X-rays from a CT scan may be used to provide information directly related to attenuation coefficients of the material being imaged.

However, PET-CT imaging has some limitations. One disadvantage is that CT provides only limited soft tissue contrast and exposes the imaged subject to significant radiation dose. To overcome these limitations, recent work has combined PET with MRI. PET-MRI reduces the amount of radiation exposure to the subject, and has shown very promising results, including excellent soft tissue contrast. Unlike CT data, however, MRI data does not directly relate to the attenuation of photons. It may be possible to generate an attenuation map based on MRI data by producing a tissue classification or pseudo-CT image from which an attenuation map can be produced.

Segmentation of MRI data is crucial for attenuation correction of PET imaging, as well as other tasks such as automated bone metastasis detection. Once structures (e.g., bone) are detected and segmented, known attenuation values may be used to generate an attenuation map for PET image reconstruction. One problem with segmenting structures such as the cortical bone, however, is that it produces no signal in MRI, and is therefore ambiguous with air. This makes primitive detection and segmentation algorithms inaccurate, and therefore insufficient for the task.

Therefore, there is a need for improved systems and methods for segmentation in medical imaging.

SUMMARY

The present disclosure relates to a framework for facilitating image processing. In accordance with one aspect, the framework receives first image data acquired by a first modality and one or more articulated models. The one or more articulated models may include at least one section image acquired by the first modality and aligned with a local image acquired by a second modality. The framework may align an anatomical region of the first image data with the section image and non-rigidly register a first region of interest extracted from the section image with a second region of interest extracted from the aligned anatomical region. To generate a segmentation mask of the anatomical region, the registered first region of interest may be inversely mapped to a subject space of the first image data.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by refer

DETAILED DESCRIPTION

Figure 1:
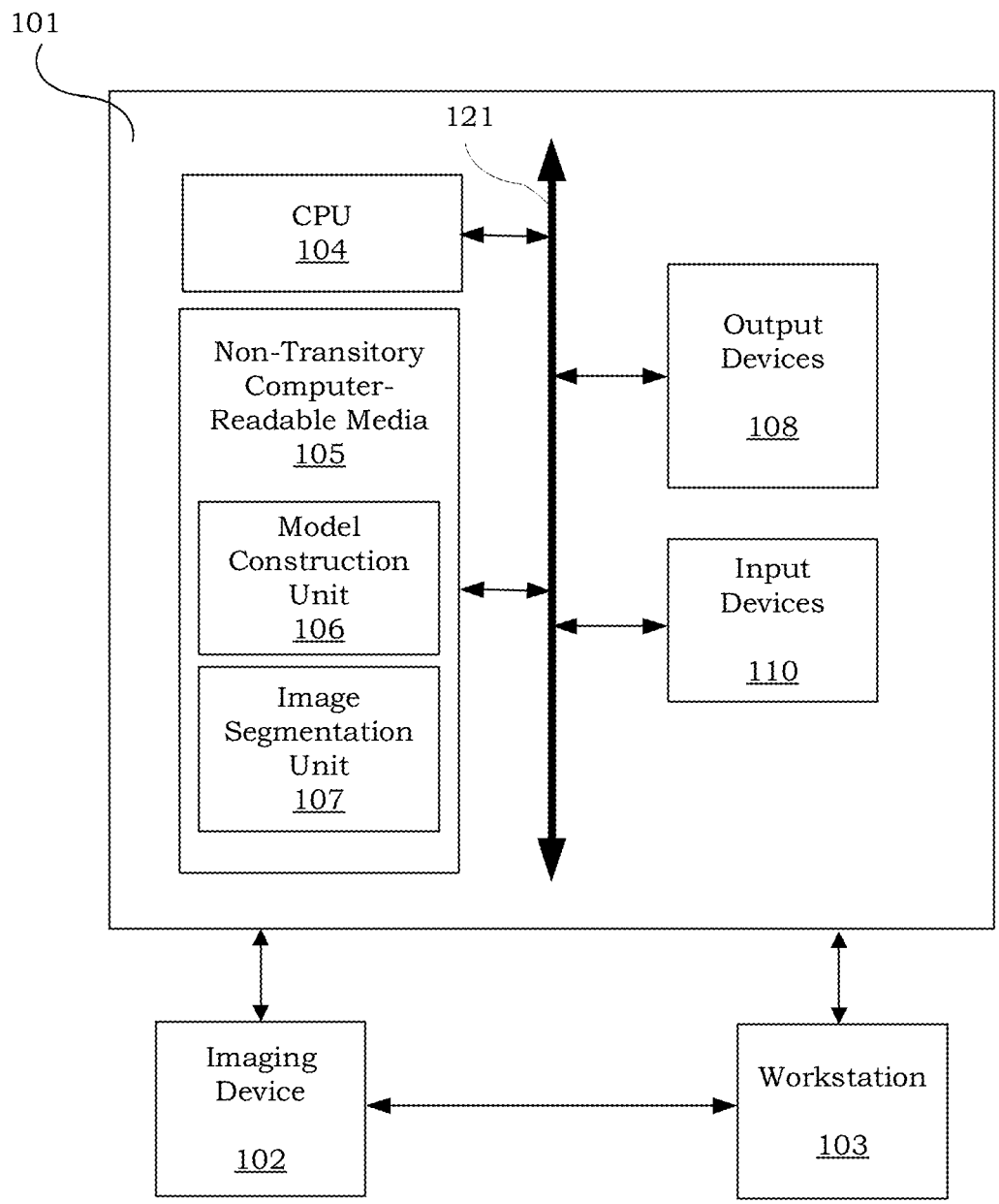
- FIG. 1 shows an exemplary computer system.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of a radiosurgery or radiotherapy procedure, which may include times when the radiation source is either on or off. From time to time, for convenience of description, CT imaging data may be used herein as an exemplary imaging modality. It will be appreciated, however, that data from any type of imaging modality including, but not limited to, X-Ray radiographs, MRI, CT, PET (positron emission tomography), PET-CT, SPECT, SPECT-CT, MR-PET, 3D ultrasound images or the like may also be used in various embodiments of the invention.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system's memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

As used herein, the term "image" refers to multi-dimensional data composed of discrete image elements (e.g., pixels for 2-D images and voxels for 3-D images). The image may be, for example, a medical image of a subject collected by computed tomography, magnetic resonance imaging, ultrasound, or any other medical imaging system known to one of skill in the art. The image may also be provided from non-medical contexts, such as, for example, remote sensing systems, electron microscopy, etc. The methods of the inventions can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of two or three mutually orthogonal axes. The terms "digital" and "digitized" as used herein will refer to images or volumes, as appropriate, in a digital or digitized format acquired via a digital acquisition system or via conversion from an analog image.

A framework for image processing is described herein. In accordance with one aspect, the framework constructs one or more articulated models (or atlases) from a first image dataset (e.g., CT) and adapts the shapes of the models to anatomical regions (e.g., bone structures) derived from a second image dataset (e.g., MR) using registration techniques. The first and second image datasets may be acquired by different imaging modalities (e.g., CT and MR respectively). The registration techniques may be "anatomy-aware" by focusing on the semantics or meaning and/or relation between anatomical regions of the object of interest. The registration techniques may also be "articulated" by processing one anatomical region at a time, and attaching multiple anatomical regions of the object of interest using an articulation model.

In accordance with another aspect, the framework uses constructed articulated models to segment image data acquired by a modality (e.g., MR) common to the second image dataset. Registration techniques are applied to adapt the shapes of anatomical regions in the image data to the articulated models to generate a segmentation mask. Local learning may further be used to improve local accuracy of the resulting segmentation mask. More particularly, a local predictor may be learned to refine the segmentation mask. Such predictor may be patient-specific and local, and therefore advantageously invariant to cross-patient and intra-patient variations. These exemplary advantages and features will be described in more details in the following description.

FIG. 1 is a block diagram illustrating an exemplary imaging system 100. The imaging system 100 includes a computer system 101 for implementing the framework as described herein. The computer system 101 may further be connected to an imaging device 102 and a workstation 103, over a wired or wireless network. The imaging device 102 may be a radiology scanner such as a magnetic resonance (MR) scanner, PET/MR, X-ray or a CT scanner.

Computer system 101 may be a desktop personal computer, a portable laptop computer, another portable device, a mini-computer, a mainframe computer, a server, a storage system, a dedicated digital appliance, or another device having a storage sub-system configured to store a collection of digital data items. In one implementation, computer system 101 comprises a processor or central processing unit (CPU) 104 coupled to one or more non-transitory computer-readable media 105 (e.g., computer storage or memory), output devices 108 (e.g., monitor, display, printer, etc.) and various input devices 110 (e.g., mouse, keyboard, touch pad, voice recognition module, etc.) via an input-output interface 121. Computer system 101 may further include support circuits such as a cache, a power supply, clock circuits and a communications bus. Even further, computer system 101 may be provided with a graphics controller chip, such as a graphics processing unit (GPU) that supports high performance graphics functions.

It is to be understood that the present technology may be implemented in various forms of hardware, software, firmware, special purpose processors, or a combination thereof. In one implementation, the techniques described herein are implemented by model construction unit 106 and image segmentation unit 107. Model construction unit 106 and image segmentation unit 107 may include computer-readable program code tangibly embodied in non-transitory computer-readable media 105. Non-transitory computer-readable media 105 may include random access memory (RAM), read only memory (ROM), magnetic floppy disk, flash memory, and other types of memories, or a combination thereof. The computer-readable program code is executed by CPU 104 to control and/or process image data from imaging device 102.

As such, the computer system 101 is a general-purpose computer system that becomes a specific-purpose computer system when executing the computer readable program code. The computer-readable program code is not intended to be limited to any particular programming language and implementation thereof. It will be appreciated that a variety of programming languages and coding thereof may be used to implement the teachings of the disclosure contained herein. Computer system 101 may also include an operating system and microinstruction code. The various techniques described herein may be implemented either as part of the microinstruction code or as part of an application program or software product, or a combination thereof, which is executed via the operating system. Various other peripheral devices, such as additional data storage devices and printing devices, may be connected to the computer system 101.

The workstation 103 may include a computer and appropriate peripherals, such as a keyboard and display, and can be operated in conjunction with the entire system 100. For example, the workstation 103 may communicate with the imaging device 102 so that the image data collected by the imaging device 102 can be rendered at the workstation 103 and viewed on the display. The workstation 103 may include a user interface that allows a radiologist or any other skilled user (e.g., physician, technician, operator, scientist, etc.), to manipulate the image data. For example, a user may identify structures or regions of interest in the image data, or annotate the structures or regions of interest using predefined descriptors via the user interface. Further, the workstation 103 may communicate directly with computer system 101 to display processed image data. For example, a radiologist can interactively manipulate the displayed representation of the processed image data and view it from various viewpoints and in various reading modes.

Figure 2:
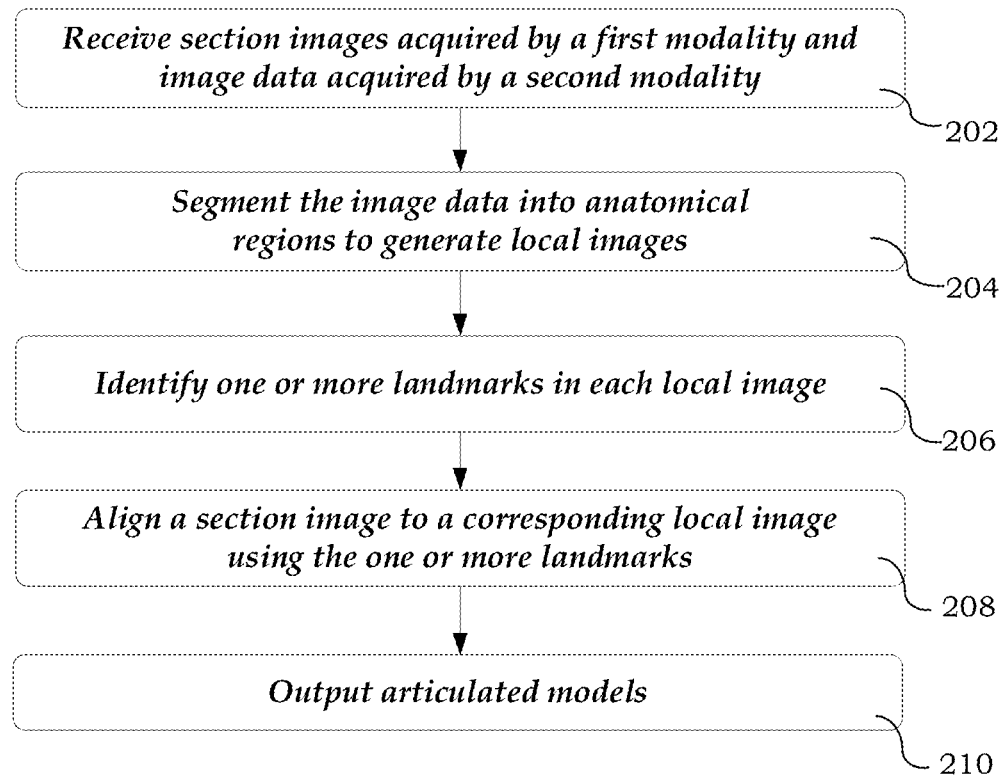
FIG. 2 shows an exemplary method of constructing articulated models.

FIG. 2 shows an exemplary method 200 of constructing articulated models. In some implementations, the method 200 is performed offline (e.g., pre-operatively, before a surgical intervention or procedure is performed on a subject or patient). It should be noted that the steps of the method 200 may be performed in the order shown or a different order. Furthermore, different, additional or fewer steps may be implemented. Even further, the method 200 may be implemented with the system 100 of FIG. 1, a different system, or a combination thereof.

At 202, model construction unit 106 receives image data and section images of an object of interest. In some implementations, the object of interest is a bone structure. Other types of objects of interest, including non-bone structures, are also possible. The image data may represent the whole object of interest, and the section images represent different anatomical regions of the object of interest. The anatomical regions are anatomically meaningful sections (e.g., right femur, left femur, skull, upper vertebrae, etc.) of the object of interest.

The section images are acquired by a first modality, while the image data is acquired by a second modality. In some implementations, the first and second modalities are the same (e.g. MR). Alternatively, the first and second modalities are different. For example, the section images are acquired by MR (e.g., in-phase MR), while the image data is acquired by CT. Other types of imaging modalities are also possible. The section images and image data may be acquired from one subject (e.g., a patient). Alternatively, the section images and image data may be represent average images acquired from multiple subjects.

Figure 3:
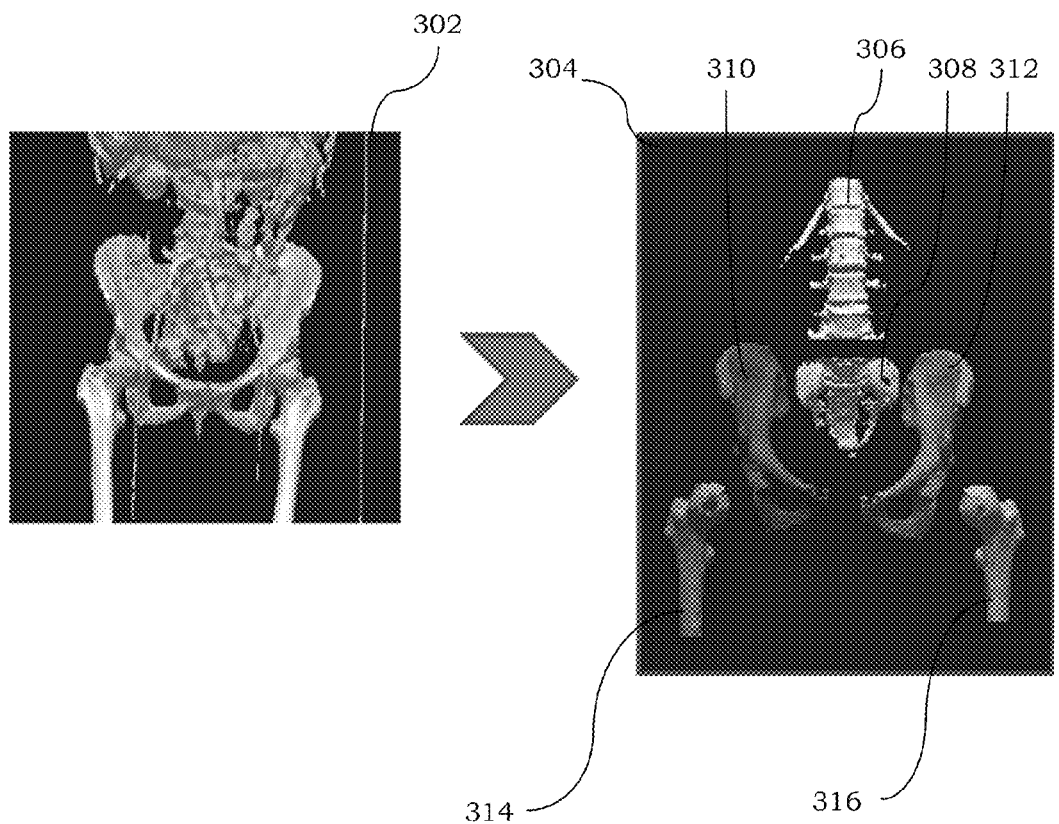
FIG. 3 shows an exemplary image of a pelvic and hip bone structure.

At 204, model construction unit 106 segments the image data into anatomical regions to generate local images. As discussed previously, the anatomical regions are isolated anatomically meaningful sections of the object of interest. The segmentation process finds the voxels of the area that belong to a particular anatomical region based on the expected shape and size of the anatomical region (e.g., femur, skull, upper vertebrae, etc.). The segmentation process may be performed manually or semi-automatically in response to a user's input via, for example, the workstation 103. FIG. 3 shows an exemplary image 302 of a pelvic and hip bone structure. The image 302 may be segmented to generate exemplary local images 304 of isolated anatomical regions corresponding to, for example, the lumbar vertebrae 306, the sacrum 308, the right hip bone 310, the left hip bone 312, the right femur 314 and the left femur 316.

Returning to FIG. 2, at 206, model construction unit 106 identifies one or more landmarks in each local image. The landmarks in the local image may correspond to landmarks in a corresponding section image. A landmark (or semantic point) may be any easily distinguishable or anatomically meaningful point on an image. For example, a landmark can represent an apex point where an outline is convex or concave. In some implementations, the landmarks are identified by using anatomical knowledge to search the image data. This may be performed automatically, semi-automatically or manually. The landmarks may be grouped and/or annotated by, for example, a label, a graphical point or any other indicator.

At 208, model construction unit 106 aligns a section image to the corresponding local image based on correspondence between the one or more landmarks in the section image and the one or more landmarks in the local image. The section image and the corresponding local image represent the same anatomical region. Alignment of the images involves a process known as registration. Rigid (e.g., linear transformation) or deformable (e.g., similarity measure) registration may be performed to align the images. Such registration may be performed manually, semi-automatically or automatically.

Figure 4:
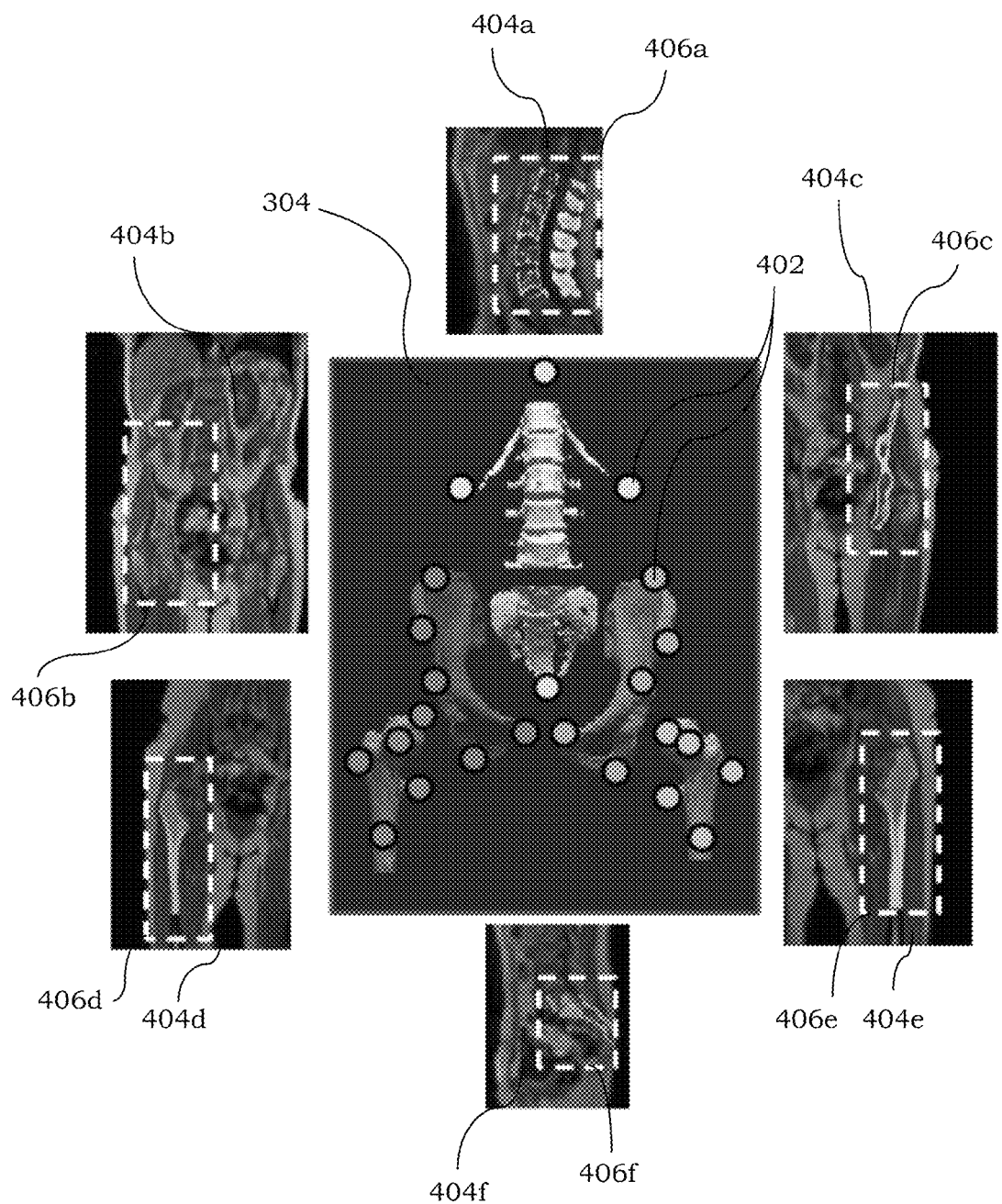
FIG. 4 illustrates an exemplary registration of multiple section images with local images.

FIG. 4 illustrates an exemplary registration of multiple section images 404*a-f* with local images 304. More particularly, local images 304, including groups of annotated landmarks 402 corresponding to different anatomical regions (e.g., lumbar vertebrae, sacrum, right and left hip bones, right and left femurs, etc.), are shown. Each section image 404*a-f* may be rigidly registered with a corresponding local image using the corresponding group of landmarks 402 within the local image. As shown, the anatomical regions 406*a-f* in the section images 404*a-f* are optimally aligned with the corresponding anatomical regions in the local images 304.

Returning to FIG. 2, at 210, model construction unit 106 outputs the constructed articulated models. Each articulated model (or atlas) may include the local image of the isolated anatomical region, the corresponding annotated landmarks associated with the anatomical region, and the corresponding aligned section image. The constructed articulated models may be used to segment image data acquired by the first modality (e.g., MR).

Figure 5:
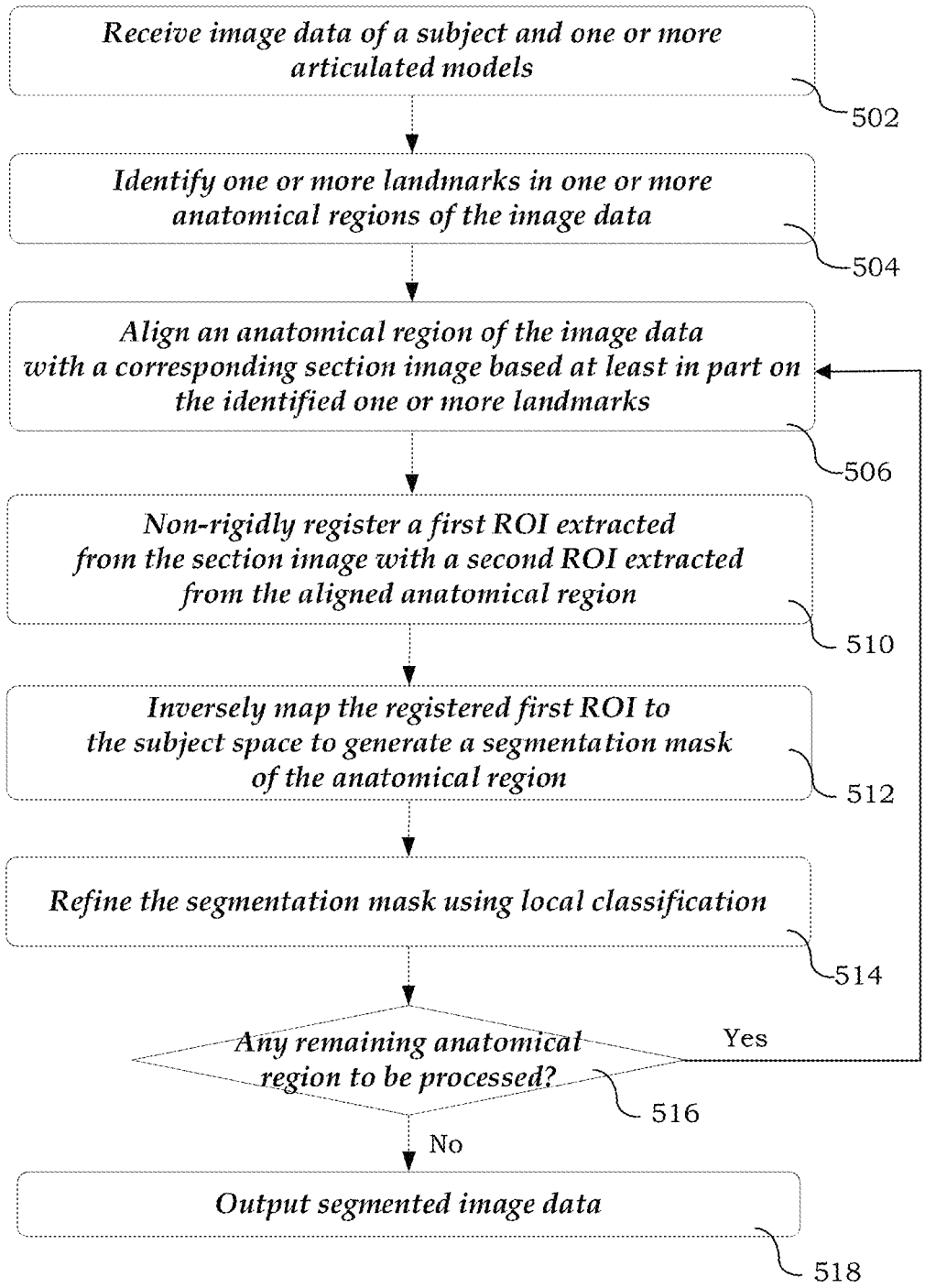
FIG. 5 shows an exemplary method of segmenting image data using the constructed articulated models.

FIG. 5 shows an exemplary method 500 of segmenting image data using the constructed articulated models. In some implementations, the method 500 is performed online (e.g., intra-operatively while a surgical intervention or procedure is performed on a subject or patient). It should be noted that the steps of the method 500 may be performed in the order shown or a different order. Furthermore, different, additional or fewer steps may be implemented. Even further, the method 500 may be implemented with the system 100 of FIG. 1, a different system, or a combination thereof.

At 502, image segmentation unit 107 receives articulated models constructed using, for instance, the method 200 as previously described with reference to FIG. 2. Each articulated model may include a local image of an isolated anatomical region, the corresponding annotated landmarks associated with the anatomical region, and the corresponding aligned section image of the anatomical region. The image segmentation unit 107 may further receive image data of a subject (e.g., patient) acquired by, for example, imaging device 102. The image data of the subject may be acquired at least in part by the same first modality as the aligned section images provided by the articulated models.

In some implementations, the image data includes a Dixon imaging sequence or related sequence derived from MR images. A Dixon image is an image acquired using the Dixon technique, an imaging technique for creating MR images of water only and fat only. More particularly, the Dixon technique is capable of computing pure fat and pure water images from MR raw data making use of the defined difference in precession times between bound water protons and bound fat protons. It should be appreciated that other types of image data are also useful.

At 504, image segmentation unit 107 identifies one or more landmarks in one or more anatomical regions of the image data. In some implementations, the landmarks are identified by using anatomical knowledge to search the image data. This may be performed automatically, semi-automatically or manually. The landmarks may be annotated by, for example, a label, a graphical point or any other indicator. Additionally, the landmarks may be grouped into one or more anatomical regions.

Figure 6:
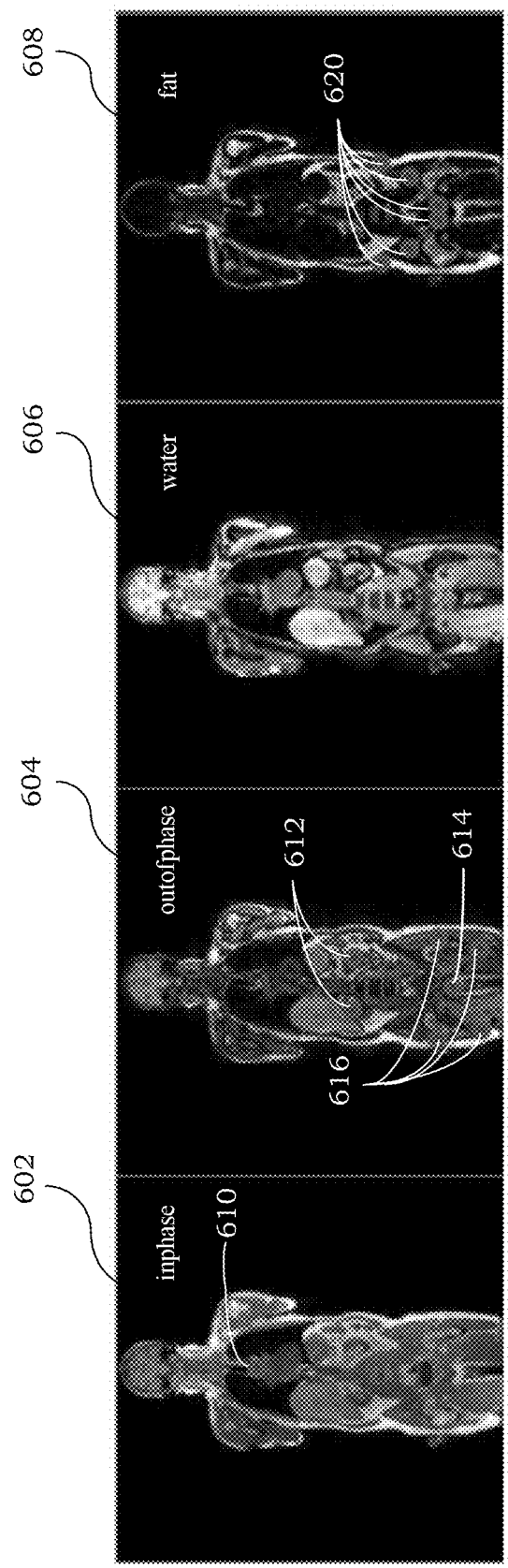
FIG. 6 shows exemplary landmarks identified on Dixon images.

FIG. 6 shows exemplary landmarks identified on Dixon images. More particularly, a Dixon in-phase image 602, a Dixon out-of-phase image 604, a Dixon water image 606 and a Dixon fat image 608 acquired from a patient are shown. Landmarks corresponding to various anatomical regions (e.g., carina, kidney, coccyx, femur, pelvis, etc.) are identified in the images 602-608. For example, a carina landmark 610 is identified in the Dixon in-phase image 602; kidney landmarks 612, coccyx landmark 614 and femur landmarks 616 are identified in the Dixon out-of-phase image 604; and pelvis landmarks 620 are identified in the Dixon fat image 608.

Figure 7:
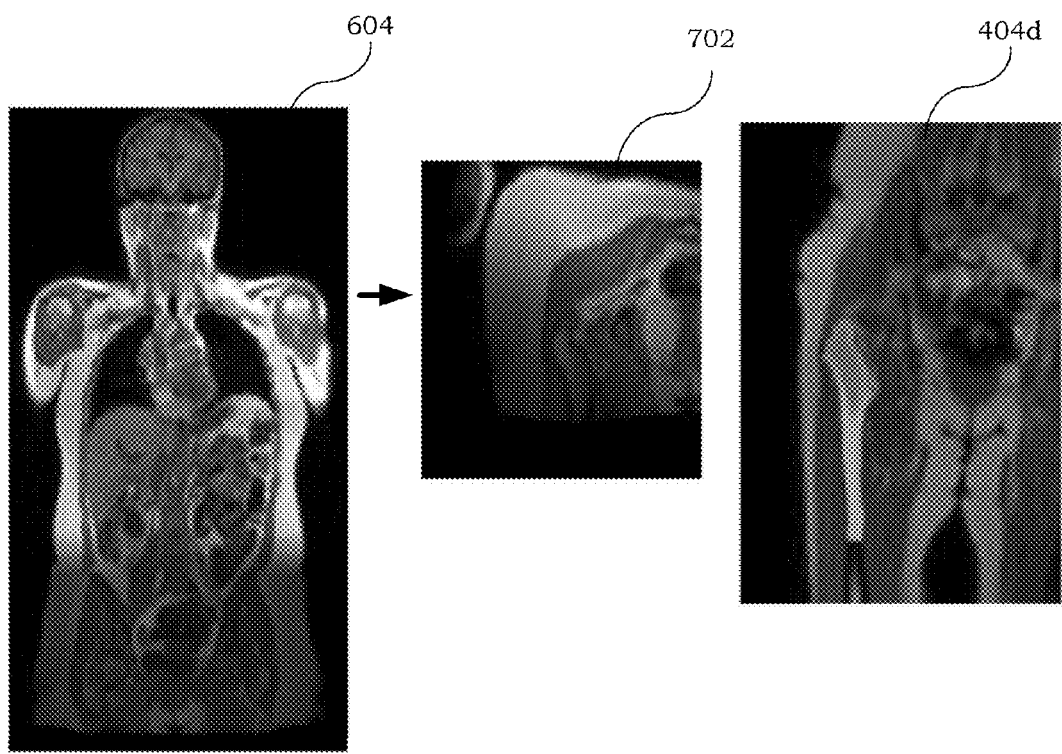
FIG. 7 illustrates an exemplary rigid registration of a patient's image with the corresponding section image.

Returning to FIG. 5, at 506, image segmentation unit 107 aligns at least one anatomical region with a corresponding section image selected from the articulated models. The alignment may be performed by using a rigid or deformable registration technique based at least in part on the previously identified landmarks. For example, pairs of landmarks from the anatomical region and the section image may be used to derive a transformation matrix (e.g., linear, similarity or affine transformations) for aligning the anatomical region with the section image. FIG. 7 illustrates an exemplary rigid registration of a patient's image 604 with the corresponding section image 404*d*. More particularly, the right femur region of the patient's image 604 is extracted and rigidly registered with the corresponding section image 404*d*, resulting in the aligned image 702.

At 510, image segmentation unit 107 non-rigidly registers a first region of interest (ROI) extracted from the section image with a second ROI extracted from the aligned anatomical region. This serves to adapt the shape of the first ROI (from the model) to the shape of the second ROI (from the current subject). The first and second ROIs may be extracted around the identified landmarks in the section image and the aligned anatomical region respectively.

Figure 8:
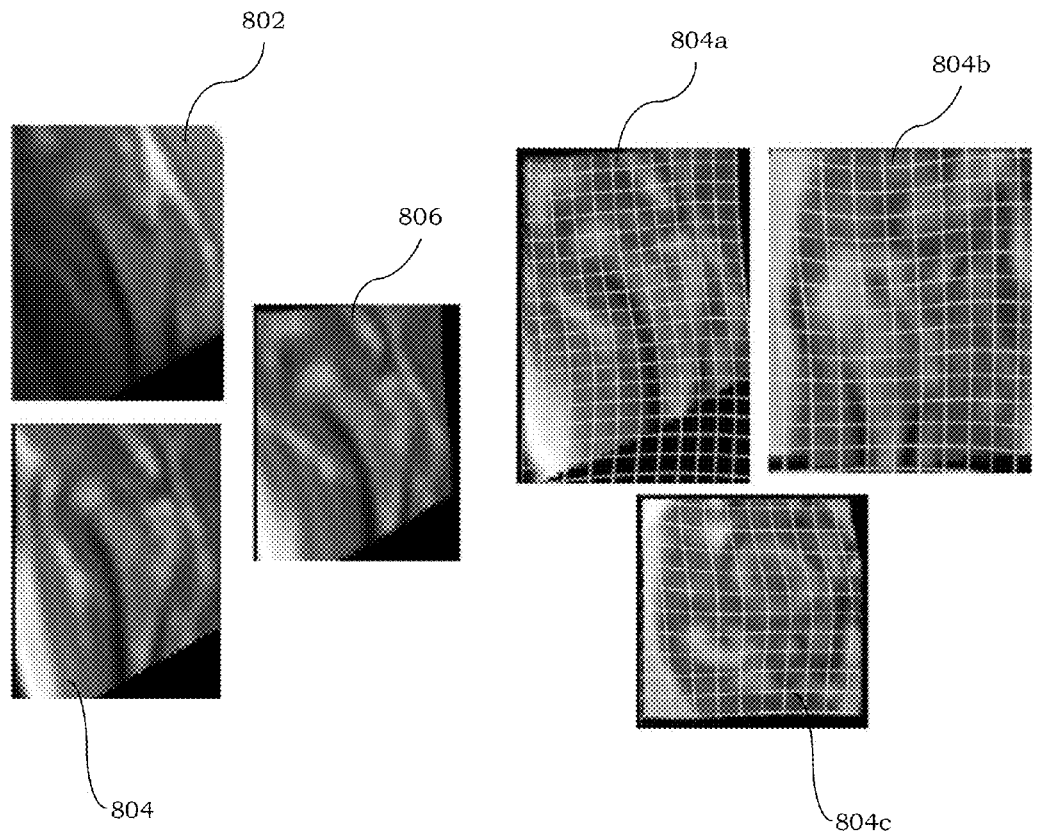
FIG. 8 illustrates an exemplary non-rigid registration process.

FIG. 8 illustrates an exemplary non-rigid registration process. As shown, a first ROI 804 is extracted from the section image, and a second ROI 802 is extracted from a previously aligned anatomical region of the patient's image. The second ROI 802 serves as the reference image for the non-rigid registration. The non-rigid transformation may be performed to locally deform or warp the first ROI 804 to align with the second ROI 802 to generate the deformed image 806. Intermediate images 804*a-c* generated during the transformation are shown. The non-rigid transformation may include, for instance, diffeomorphic deformations, free-form deformation, thin-plate spline deformations, B-spline deformations, etc. Registration parameters (e.g., level of elasticity or regularization, convergence criteria, similarity measures, etc.) and grid size may be adapted particularly for each section image. These parameters are adapted manually or semi-automatically at the time of the design or training of the framework.

Figure 9:
FIG. 9 shows exemplary views of a subject's segmented image data.

Returning to FIG. 5, at 512, image segmentation unit 107 inversely maps the registered or warped first ROI to the space of the subject's image data to generate a segmentation mask of the anatomical region (e.g., cortical bone). This may be performed by inverting the transformation matrix used in step 506. FIG. 9 shows exemplary views of the subject's segmented image data. More particularly, the coronal view 902, the sagittal view 904 and the transverse view 906 of the segmented image data are shown. The cortical bone segmentation masks 912, 914 and 916 are shown in the respective views 902, 904 and 906.

Returning to FIG. 5, at 514, image segmentation unit 107 applies a local classification (or learning) technique to refine the segmentation mask. Local classification techniques may be applied to fix errors in registration and improve local accuracy. The segmentation mask may be refined locally by majority. Local classification techniques may include, for example, semi-supervised learning (e.g., partially labeled classification) or location-adaptive local appearance learning (e.g., an algorithm that knows pitfalls near the cerebrospinal fluid). In addition, the local classification technique (e.g., linear regression) may use the current anatomical region segmentation mask obtained in step 512 as a prior and constraint. The present framework may utilize a hierarchical method of registration, which brings the bone segmentation mask (from atlas) close to the ground truth so that the majority of voxels are correctly labeled.

Figure 10:
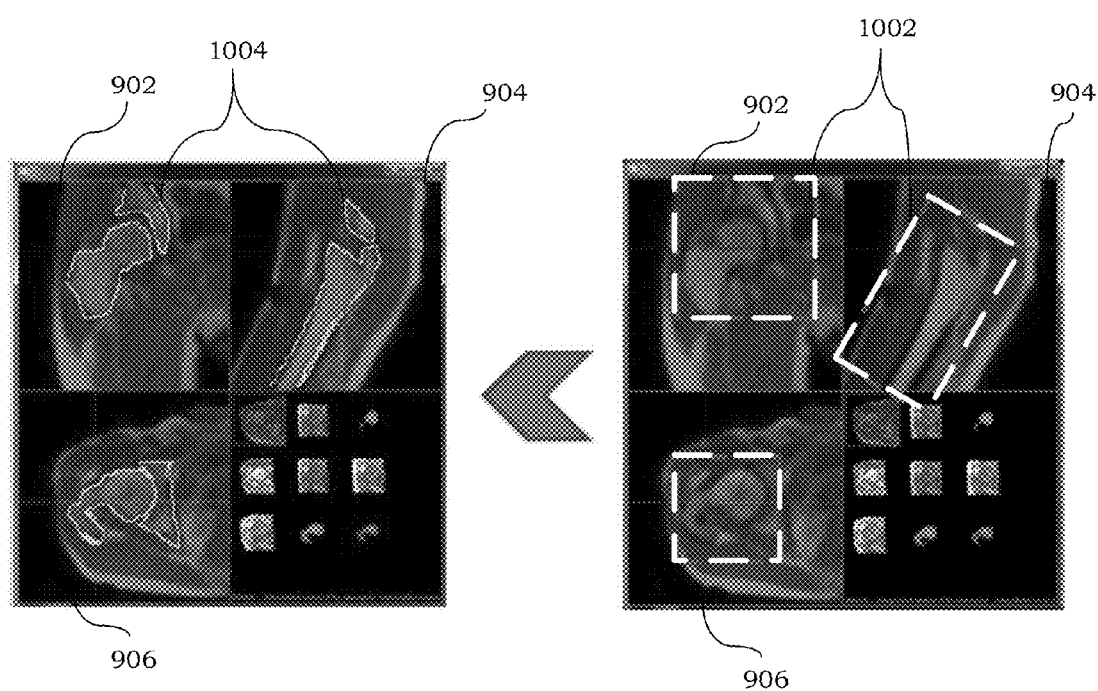
FIG. 10 illustrates an exemplary local classification technique.

FIG. 10 illustrates an exemplary local classification technique. The coronal view 902, the sagittal view 904 and the transverse view 906 of the segmented image data are shown. In accordance with some implementations, a learning-based MR bone predictor is trained to exploit appearance characteristics in MR. The local bone predictor may refine the bone mask 1002 within local regions 902, 904 and 906 to generate the refined bone masks 1004.

Figure 11:
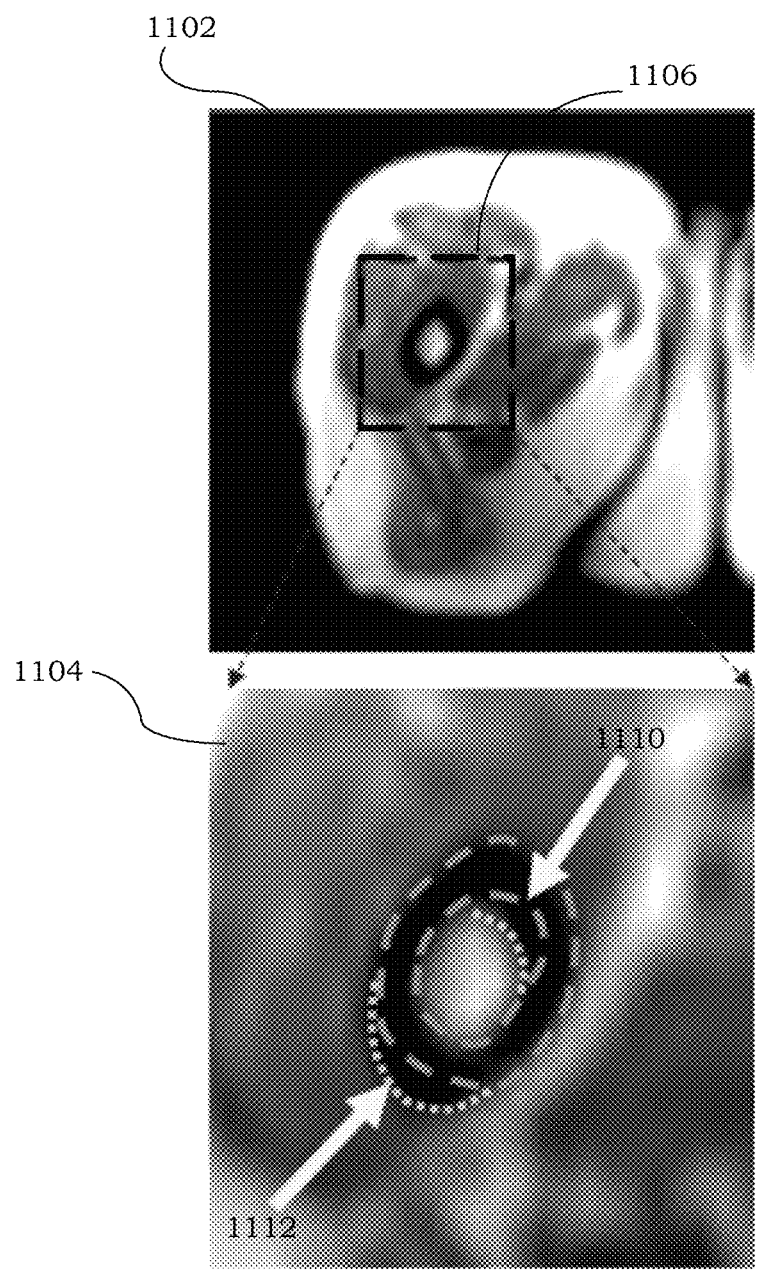
FIG. 11 is another illustration of the exemplary local classification technique.

FIG. 11 is another illustration of the exemplary local classification technique. First, a local bone predictor is trained using the current bone segmentation mask within local region 1106 of the subject's image 1102. Next, the current bone mask is refined using the trained local bone predictor. These two steps may be iteratively performed until a terminating criterion is satisfied. As shown in the magnified image 1104 of the local region 1106, the initial bone mask 1110 is refined by this iterative process until the final bone mask 1112 is generated.

In the art, it has been difficult to learn a 'general' and 'global' bone predictor because MR intensities of cortex bone vary a lot both across patients (due to, e.g., different machines, coil positioning, etc.) and within a patient (due to, e.g., field inhomogeneity, bio-chemical differences across bones, etc.). The present framework trains and uses a bone predictor that is advantageously invariant to cross-patient variations (i.e., patient-specific) and invariant to intra-patient variations (i.e., local).

Returning to FIG. 5, at 516, image segmentation unit 107 determines if any remaining anatomical region is to be processed. If yes, steps 506-514 are repeated to process the next anatomical region. If no, the method 500 continues to 518.

Figure 12:
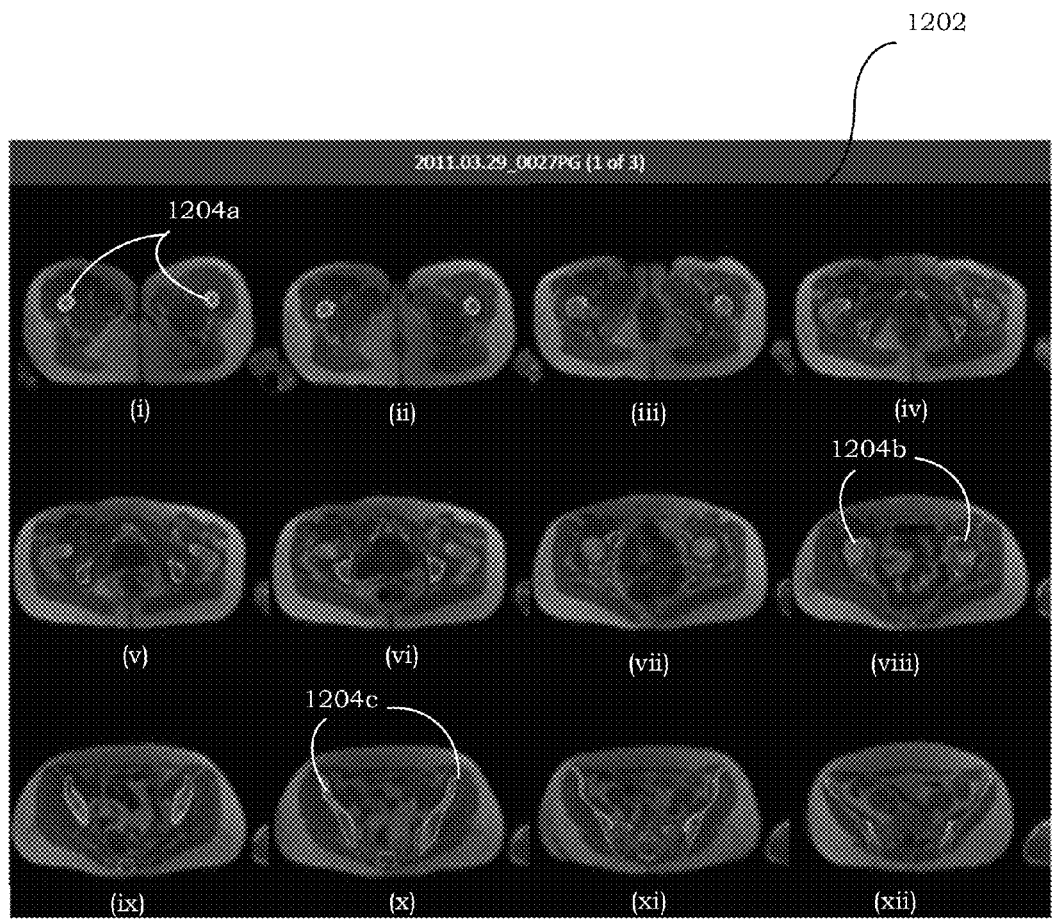
FIG. 12 shows exemplary segmented image data.

At 518, image segmentation unit 107 outputs the segmented image data. FIG. 12 shows exemplary segmented image data 1202. More particularly, segmented image data 1202 includes a series of images (i) through (xii) that represent various axial views of a patient's hip, starting from the lower part to the upper part of the hip. The image data 1202 includes various exemplary segmentation masks 1204*a*-*c* (e.g., lower hip bone, femur, pelvis, etc.) generated by the present framework.

While the present invention has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

The invention claimed is:

1. A computer-implemented method of image segmentation, comprising:
   (i) constructing articulated models including individual section images representing related anatomical regions of an object of interest, wherein the section images are acquired by a first modality and aligned with local images of the related anatomical regions acquired by a second modality, wherein the first and second modalities are different, wherein at least one of the articulated models comprises one of the local images, corresponding annotated landmarks and a corresponding one of the aligned section images;
   (ii) receiving first image data acquired by the first modality;
   (iii) aligning an anatomical region of the first image data with a corresponding one of the aligned section images;
   (iv) non-rigidly registering a first region of interest extracted from the corresponding aligned section image with a second region of interest extracted from the aligned anatomical region;
   (v) generating a segmentation mask of the anatomical region by inversely mapping the registered first region of interest to a subject space of the first image data; and
   repeating steps (iii), (iv) and (v) to segment another anatomical region of the first image data.

2. The method of claim 1 wherein the anatomical region comprises an isolated bone region.

3. The method of claim 1 wherein aligning the anatomical region of the first image data with the section image comprises identifying one or more landmarks in the anatomical region, and using the one or more landmarks to align the anatomical region with the section image.

4. The method of claim 1 wherein aligning the anatomical region of the first image data with the section image comprises performing a rigid registration on the anatomical region with the section image.

5. The method of claim 1 wherein aligning the anatomical region of the first image data with the section image comprises performing a deformable registration on the anatomical region with the section image.

6. The method of claim 1 wherein non-rigidly registering the first region of interest with the second region of interest comprises adapting registration parameters particular to the section image.

7. The method of claim 1 further comprising applying local classification to refine the segmentation mask.

8. The method of claim 7 wherein applying the local classification to refine the segmentation mask comprises iteratively training a local predictor within a local region of the image data and refining the segmentation mask using the trained local predictor.

9. The method of claim 1 wherein constructing the articulated models comprises:
   segmenting second image data acquired by the second modality into the anatomical region to generate the local image; and
   aligning the section image with the local image.

10. A non-transitory computer-readable medium embodying a program of instructions executable by machine to perform steps for image segmentation, the steps comprising:

(i) constructing articulated models including individual section images representing related anatomical regions of an object of interest, wherein the section images are acquired by a first modality and aligned with local images of the related anatomical regions acquired by a second modality, wherein the first and second modalities are different, wherein at least one of the articulated models comprises one of the local images, corresponding annotated landmarks and a corresponding one of the aligned section images;

(ii) receiving first image data acquired by the first modality;

(iii) aligning an anatomical region of the first image data with a corresponding one of the aligned section images;

(iv) non-rigidly registering a first region of interest extracted from the corresponding aligned section image with a second region of interest extracted from the aligned anatomical region;

(v) generating a segmentation mask of the anatomical region by inversely mapping the registered first region of interest to a subject space of the first image data; and repeating steps (iii), (iv) and (v) to segment another anatomical region of the first image data.

11. An image processing system, comprising:

a non-transitory memory device for storing computer-readable program code; and a processor in communication with the memory device, the processor being operative with the computer-readable program code to perform steps for constructing articulated models, the steps comprising receiving individual section images acquired by a first modality and first image data acquired by a second modality, wherein the section images represent different related anatomical regions of an object of interest and the first image data represents the object of interest, wherein the first and second modalities are different, segmenting the first image data into the different anatomical regions to generate local images, identifying one or more landmarks in at least one of the local images, aligning the section images with the local images using the one or more landmarks, and outputting articulated models including the aligned section images and segmenting second image data acquired by the first modality by using the articulated models including the aligned section images.

12. The system of claim 11 wherein the first modality comprises magnetic resonance imaging (MRI) and the second modality comprises computed tomographic (CT) imaging.

13. The system of claim 11 wherein the anatomical regions comprise isolated bone regions.

14. The system of claim 11 wherein the processor is operative with the computer-readable program code to align the section images with the local images based on correspondence between one or more landmarks in a section image and one or more landmarks in a local image.

15. The system of claim 14 wherein the processor is operative with the computer-readable program code to align the section images with the local images by performing a non-rigid transformation using the landmarks.

16. The system of claim 14 wherein the processor is operative with the computer-readable program code to align the section images with the local images by performing a rigid transformation using the landmarks.

* * * * *